United States Patent [19]

Hurnaus et al.

[11] Patent Number: 4,486,433
[45] Date of Patent: Dec. 4, 1984

[54] FUSED-RING AMINO-PYRAZINES AS BRADYCARDIACS

[75] Inventors: Rudolf Hurnaus; Gerhart Griss, both of Biberach; Robert Sauter, Laupheim; Wolfgang Grell, Biberach, all of Fed. Rep. of Germany; Walter Kobinger; Ludwig Pichler, both of Vienna, Austria

[73] Assignee: Dr. Karl Thomae Gesellschaft mit beschränkter Haftung, Biberach, Fed. Rep. of Germany

[21] Appl. No.: 501,437

[22] Filed: Jun. 6, 1983

Related U.S. Application Data

[62] Division of Ser. No. 297,024, Aug. 27, 1981, Pat. No. 4,409,220.

[30] Foreign Application Priority Data

Sep. 2, 1980 [DE] Fed. Rep. of Germany ....... 3032994

[51] Int. Cl.³ ................. C07D 471/04; C07D 487/04; A61K 31/495; A61K 31/55
[52] U.S. Cl. ................................ 424/250; 260/243.3
[58] Field of Search .................... 544/350; 260/243.3; 424/250

[56] References Cited

FOREIGN PATENT DOCUMENTS

| | | |
|---|---|---|
| 3016 | 7/1979 | European Pat. Off. . |
| 2357253 | 5/1975 | Fed. Rep. of Germany . |
| 2519258 | 11/1976 | Fed. Rep. of Germany . |
| 2617101 | 11/1977 | Fed. Rep. of Germany . |
| 1009477 | 11/1965 | United Kingdom . |
| 2084135 | 4/1982 | United Kingdom ................ 544/350 |

*Primary Examiner*—Mark L. Berch
*Attorney, Agent, or Firm*—Hammond & Littell, Weissenberger & Dippert

[57] ABSTRACT

Compounds of the formula

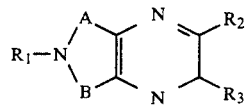

wherein

A and B, which may be the same or different, each represent methylene, (alkyl of 1 to 3 carbon atoms)-methylene, ethylene or (alkyl of 1 to 3 carbon atoms)-ethylene;

$R_1$ is hydrogen, alkyl of 1 to 6 carbon atoms, cycloalkyl of 3 to 7 carbon atoms, alkenyl of 3 to 6 carbon atoms, phenyl-(alkyl of 1 to 3 carbon atoms), halophenyl-(alkyl of 1 to 3 carbon atoms), alkanoyl of 1 to 3 carbon atoms, phenyl-(alkanoyl of 1 to 3 carbon atoms), halophenyl-(alkanoyl of 1 to 3 carbon atoms), alkoxycarbonyl of 2 to 4 carbon atoms, aralkoxycarbonyl of 8 to 10 carbon atoms or phenyl;

one of $R_2$ and $R_3$ is amino and the other is hydrogen, chlorine, bromine, alkyl of 1 to 3 carbon atoms, alkoxy of 1 to 3 carbon atoms, alkoxycarbonyl of 2 to 4 carbon atoms, phenyl or halophenyl;

and non-toxic, pharmacologically acceptable acid addition salts thereof. The compounds as well as their salts are useful as bradycardiacs.

8 Claims, No Drawings

FUSED-RING AMINO-PYRAZINES AS BRADYCARDIACS

This is a division of copending application Ser. No. 297,024, filed Aug. 27, 1981, now U.S. Pat. No. 4,409,220.

This invention relates to novel fused-ring aminopyrazines and acid addition salts thereof, to methods of preparing these compounds, to pharmaceutical compositions containing them as active ingredients, and to methods of using them as bradycardiacs.

More particularly, the present invention relates of a novel class of compounds represented by the formula

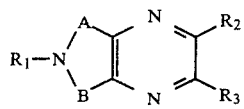

(I)

wherein

A and B, which may be the same or different, each represent methylene, (alkyl of 1 to 3 carbon atoms)-methylene, ethylene or (alkyl of 1 to 3 carbon atoms)-ethylene;

$R_1$ is hydrogen, alkyl of 1 to 6 carbon atoms, cycloalkyl of 3 to 7 carbon atoms, alkenyl of 3 to 6 carbon atoms, phenyl-(alkyl of 1 to 3 carbon atoms), halophenyl-(alkyl of 1 to 3 carbon atoms), alkanoyl of 1 to 3 carbon atoms, phenyl-(alkanoyl of 1 to 3 carbon atoms), halophenyl-(alkanoyl of 1 to 3 carbon atoms), alkoxycarbonyl of 2 to 4 carbon atoms, aralkoxycarbonyl of 8 to 10 carbon atoms or phenyl;

one of $R_2$ and $R_3$ is amino and the other is hydrogen, chlorine, bromine, alkyl of 1 to 3 carbon atoms, alkoxy of 1 to 3 carbon atoms, alkoxycarbonyl of 2 to 4 carbon atoms, phenyl or halophenyl;

and non-toxic, pharmacologically acceptable acid addition salts thereof.

Examples of specific embodiments of A, B, $R_1$, $R_2$ and $R_3$ are the following:

A and B, which may be the same or different, —Methylene, methyl-methylene, ethyl-methylene, propyl-methylene, isopropyl-methylene, ethylene, methyl-ethylene, ethyl-ethylene, propyl-ethylene and isopropyl-ethylene;

$R_1$—Hydrogen, methyl, ethyl, propyl, isopropyl, butyl, isobutyl, butyl-(2), tert.butyl, pentyl, isopentyl, neopentyl, tert.pentyl, hexyl, allyl, crotonyl, penten-(2)-yl, hexen-(2)-yl, cyclopropyl, cyclobutyl, cyclopentyl, cyclohexyl, cycloheptyl, benzyl, fluorobenzyl, chlorobenzyl, bromobenzyl, 1-phenyl-ethyl, 1-(fluoro-phenyl)-ethyl, 1-(chloro-phenyl)-ethyl, 1-(bromo-phenyl)-ethyl, 2-phenyl-ethyl, 2-(fluoro-phenyl)-ethyl, 2-(chloro-phenyl)-ethyl, 2-(bromo-phenyl)-ethyl, 1-phenyl-propyl, 2-phenyl-propyl, 3-phenyl-propyl, 1-(fluoro-phenyl)-propyl, 1-(chloro-phenyl)-propyl, 2-(chloro-phenyl)-propyl, 2-(bromo-phenyl)-propyl, 3-(fluoro-phenyl)-propyl, 3-(chloro-phenyl)-propyl, 3-(bromo-phenyl)-propyl, formyl, benzoyl, fluoro-benzoyl, chloro-benzoyl, bromo-benzoyl, acetyl, phenyl-acetyl, fluorophenyl-acetyl, chlorophenyl-acetyl, bromo-phenyl-acetyl, propionyl, 2-phenyl-propionyl, 3-phenyl-propionyl, 2-(fluoro-phenyl)-propionyl, 2-(chloro-phenyl)-propionyl, 3-(chloro-phenyl)-propionyl, 3-(bromo-phenyl)-propionyl, methoxycarbonyl, ethoxycarbonyl, propoxycarbonyl, isopropoxycarbonyl, benzyloxycarbonyl, methylbenzyloxy-carbonyl, ethylbenzyloxy-carbonyl and phenyl;

$R_2$ and $R_3$—Hydrogen, chlorine, bromine, methyl, ethyl, propyl, isopropyl, methoxy, ethoxy, propoxy, isopropoxy, methoxycarbonyl, ethoxycarbonyl, propoxycarbonyl, isopropoxycarbonyl, phenyl, fluorophenyl, chloro-phenyl, bromo-phenyl or one of them amino.

A preferred subgenus is constituted by those compounds of the formula I wherein

A and B, which may be the same or different, each represent methylene, ethylene, or methyl-ethylene;

$R_1$ is hydrogen, alkyl of 1 to 4 carbon atoms, cycloalkyl of 3 to 6 carbon atoms, phenyl (alkyl of 1 to 3 carbon atoms), chlorophenyl-(alkyl of 1 to 3 carbon atoms), formyl, phenyl-formyl, chlorophenyl-formyl, acetyl, phenyl-acetyl, chlorophenyl-acetyl, ethoxycarbonyl or phenyl;

$R_2$ is hydrogen, chlorine, bromine, methyl, ethyl, methoxy, phenyl or ethoxycarbonyl; and $R_3$ is amino;

and non-toxic, pharmacologically acceptable acid addition salts thereof.

An especially preferred subgenus is constituted by those compounds of the formula I wherein A is methylene or ethylene;

B is ethylene;

$R_1$ is methyl, ethyl, isopropyl, cyclopropyl, cyclobutyl or allyl;

$R_2$ is methyl, hydrogen, chlorine or bromine; and $R_3$ is amino;

and non-toxic, pharmacologically acceptable acid addition salts thereof.

A particularly preferred subgenus is constituted by those compounds of the formula I wherein A and B are ethylene;

$R_1$ is methyl, ethyl, isopropyl, cyclopropyl, cyclobutyl or allyl;

$R_2$ is hydrogen; and $R_3$ is amino;

and non-toxic, pharmacologically acceptable acid addition salts thereof.

The compounds embraced by formula I may be prepared by the following methods:

Method A:

By reacting a diketone of the formula

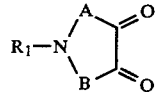

(II)

wherein A, B and $R_1$ have the same meanings as in formula I, with a 2-amino-acetamidine of the formula

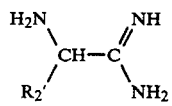

(III)

wherein $R_2'$ is hydrogen, alkyl of 1 to 3 carbon atoms, alkoxycarbonyl of 2 to 4 carbon atoms, phenyl or halophenyl.

The reaction is advantageously performed in a solvent such as water, methanol, isopropanol, water/methanol or water/dioxane, and preferably in the presence of a base such as sodium carbonate, sodium hydroxide or pyridine, at temperatures between −50° and +100° C., preferably between −30° and +50° C. Pyridine in sufficient excess may simultaneously serve as the solvent medium. The diketone may optionally be formed in situ in the reaction mixture.

Method B:
By reducing a pyrazine-N-oxide of the formula

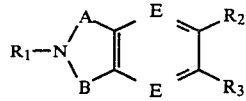
(IV)

wherein
A, B, $R_1$, $R_2$ and $R_3$ have the same meanings as in formula I, and
one E is N-oxide and the other is nitrogen or N-oxide.

The reduction is preferably carried out in a solvent such as water, water/ethanol, ethylacetate or dimethylformamide and is advantageously effected with (a) hydrogen in the presence of a hydrogenation catalyst such as platinum or palladium-on-charcoal; or (b) a metal such as iron, tin or zinc in the presence of an acid; or (c) a reducing salt such as sodium dithionite; or (d) a phosphorus trihalide such as phosphorus trichloride, at temperatures between 0° and 150° C., preferably between 25° and 100° C. The pyrazine-N-oxide starting compound may optionally be formed in situ in the reaction mixture.

Method C:
By cyclizing a compound of the formula

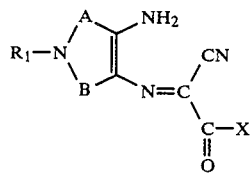
(V)

wherein
$R_1$, A and B have the same meanings as in formula I, and
X is alkoxy,
optionally followed by hydrolysis and decarboxylation of the obtained compound of the formula

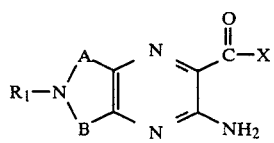
(VI)

wherein $R_1$, A, B and X have the meanings previously defined.

The cyclization is advantageously carried out in a solvent such as diethyl ether, tetrahydrofuran, ethanol or dioxane, and preferably in the presence of a base such as an alkali metal alkanolate, for instance potassium tert.butylate, at temperatures between −20° and +50° C., preferably between 0° and 25° C.

The subsequent hydrolysis and decarboxylation is performed in the presence of an acid such a hydrobromic acid or sulfuric acid, for instance 80% sulfuric acid, at temperatures between 50° and 250° C., preferably between 100° and 200° C.

Method D:
By reacting a pyrazine of the formula

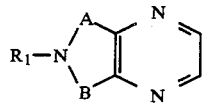
(VII)

wherein $R_1$, A and B have the same meanings as in formula I, with an alkali metal amide, preferably with sodium amide or potassium amide.

The reaction is advantageously performed in a solvent such as xylene, tetralin, or dimethylaniline, if necessary in a pressure vessel, at temperatures between 100° and 250° C., preferably between 150° and 200° C.

Method E:
By reacting an oxime of the formula

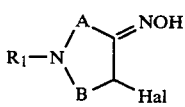
(VIIIa)

or

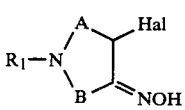
(VIIIb)

wherein
$R_1$, A and B have the same meanings as in formula I, and
Hal is chlorine, bromine or iodine,
with an α-amino-acetonitrile of the formula

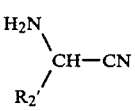
(IX)

wherein $R_2'$ is hydrogen, alkyl of 1 to 3 carbon atoms, alkoxycarbonyl of 2 to 4 carbon atoms, phenyl or halophenyl.

The reaction is advantageously performed in a solvent such as water, methanol, water/methanol, isopropanol, chloroform or dioxane, and preferably in the presence of a base such as sodium carbonate, sodium hydroxide, triethylamine or pyridine, at temperatures between −50° and +100° C., preferably between −30° and +50° C. A sufficient excess of triethylamine or pyridine may simultaneously serve as the solvent medium. The oxime starting compound may optionally be formed in situ in the reaction mixture.

A compound of the formula

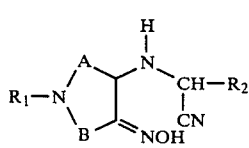
(Xa)

or

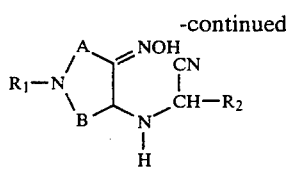
(Xb)

wherein $R_1$, $R_2$, A and B have the same meanings as in formula I, which may be formed in the reaction mixture in the course of the reaction may also subsequently be cyclized in the presence of an acid condensation agent such as polyphosphoric acid which may simultaneously serve as the solvent medium.

Method F:
By reacting a pyrazine of the formula

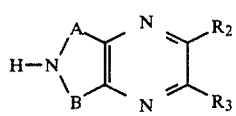
(XI)

wherein A, B, $R_2$ and $R_3$ have the same meanings as in formula I, with a compound of the formula $$R_1'-Y \qquad (XII)$$

wherein
$R_1'$ has the same meanings as $R_1$ in formula I except hydrogen and phenyl, and
Y is a nucleophilic leaving group.

Thus, when $R_1'$ is alkyl, phenylalkyl, cycloalkyl or alkenyl, Y may for example be halogen, such as chlorine, bromine or iodine, or a sulfonyloxy group such as methylsulfonyloxy, methoxysulfonyloxy or p-toluenesulfonyloxy.

When $R_1'$ is alkanoyl, phenylalkanoyl, benzoyl or alkoxycarbonyl, Y may for example be halogen such as chlorine or bromine, aryloxy such as phenoxy or nitrophenyl, or —O—$COR_1'$ such as acetoxy or ethoxycarbonyl.

When $R_1'$ is alkyl, Y may also be hydroxyl.

The reaction is advantageously performed in a solvent such as water, methanol, diethyl ether, tetrahydrofuran, dioxane, acetonitrile, chloroform, dimethylformamide or dimethylsulfoxide and optionally in the presence of an acid-binding agent such as sodium hydroxide, potassium carbonate, potassium tert.butylate, triethylamine, N-ethyl-diisopropylamine or pyridine. In sufficient excess, the three last-mentioned acid-binding agents may simultaneously serve as the solvent medium. The reaction temperature is between 0° and 150° C., preferably between 20° and 110° C. However, the reaction will also proceed in the absence of a solvent.

When Y is hydroxyl, the reaction is performed in the presence of Raney nickel and preferably at the boiling point of the alcohol of the formula $R_1'$ OH which is advantageously used as the solvent medium.

Method G:
By reacting a pyrazine of the formula

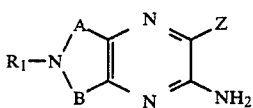
(XIII)

wherein $R_1$, A and B have the same meanings as in formula I, and
Z is a nucleophilic leaving group such as halogen, especially chlorine or bromine,
with a compound of the formula $$H-R_2'' \qquad (XIV)$$

wherein $R_2''$ is alkoxy of 1 to 3 carbon atoms, or an alkali metal salt thereof.

The reaction is advantageously performed in a solvent such as methanol, ethanol, dimethylformamide, dioxane or dichlorobenzene, but preferably in an excess of the compound of the formula XIV; optionally in a pressure vessel and preferably in the presence of an alkali metal base at temperatures between 50° and 200° C., preferably between 65° and 175° C.

If the end product of methods A to G is a compound of the formula I wherein $R_1$ is alkanoyl of 1 to 3 carbon atoms, phenyl-(alkanoyl of 1 to 3 carbon atoms), halophenyl-(alkanoyl of 1 to 3 carbon atoms), alkoxycarbonyl of 2 to 4 carbon atoms, or aralkoxycarbonyl of 8 to 10 carbon atoms, the same may be converted into the corresponding compound of the formula I wherein $R_1$ is hydrogen by hydrolysis and, if necessary, subsequent decarboxylation. The hydrolysis is advantageously performed either in the presence of an acid such as hydrochloric acid, sulfuric acid, phosphoric acid or trifluoroacetic acid, or in the presence of a base such as sodium hydroxide or potassium hydroxide in a solvent such as ethanol, water/ethanol, water/isopropanol or water/dioxane at elevated temperatures, for instance at the boiling point of the reaction mixture, or also in the absence of a solvent. The subsequent decarboxylation is effected by heating the alkali metal salt of the hydrolysis product or by heating the free acid in a strong mineral acid, such as concentrated hydrochloric acid, at temperatures between 80° and 250° C., preferably between 100° to 200° C.

If the end product of methods A to G is a compound of the formula I wherein $R_1$ is alkanoyl of 1 to 3 carbon atoms, phenyl-(alkanoyl of 1 to 3 carbon atoms), halophenyl-(alkanoyl of 1 to 3 carbon atoms), alkoxycarbonyl of 2 to 4 carbon atoms or aralkoxycarbonyl of 8 to 10 carbon atoms, the same may be converted into the corresponding compound of the formula I wherein $R_1$ is alkyl of 1 to 3 carbon atoms, phenyl-(alkyl of 1 to 3 carbon atoms) or halophenyl-(alkyl of 1 to 3 carbon atoms) by reduction. The reduction is preferably carried out with a complex metal hydride, such as lithium aluminimum hydride, in a solvent, such as diethyl ether, tetrahydrofuran or dioxane, at temperatures between 0° and 100° C., preferably at room temperature.

If the end product of methods A to G is a compound of the formula I wherein $R_1$ is benzyl or halobenzyl, the same may be converted into the corresponding compound of the formula I wherein $R_1$ is hydrogen by reaction with benzyl chloroformate and subsequent removal of the carbonate radical. The reaction with benzyl chloroformate is preferably carried out in a solvent such as chloroform, methylene chloride or benzene, optionally in the presence of triethylamine, pyridine or N-ethyl diisopropylamine, at temperaturs between 0° and 50° C. The subsequent removal of the carbonate radical is preferably effected by heating in glacial acetic acid/hydrobromic acid at 100° C., for example.

If the end product of methods A to G is a compound of the formula I wherein $R_2$ is hydrogen and $R_3$ is amino, the same may be converted into the corresponding compound of the formula I wherein $R_2$ is halogen by halogenation. The halogenation is carried out with a halogenating agent, such as chlorine or bromine, preferably in a solvent such as glacial acetic acid or chloroform, optionally in the presence of pyridine, at temperatures between 0° and 50° C., preferably at room temperature.

The compounds embraced by formula I are basic and therefore form addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, succinic acid, maleic acid, fumaric acid or the like.

The starting compounds of the formula II to XIV are either described in the literature or may be prepared by known methods.

For instance, a diketone of the formula II may be obtained by reacting a corresponding tetrahydro-bis-(trialkylsilyloxy)-azepine with bromine, copper-II-acetate or oxygen of the air in a solvent such as methanol, carbon tetrachloride, pyridine and/or dioxane at temperatures between 0° and 100° C., or by selenium dioxide oxidation of a corresponding hexahydroazepinone.

A starting compound of the formula IV may be obtained by reacting a corresponding oxime of the formula

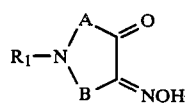 (XVa)

or

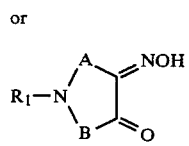 (XVb)

wherein $R_1$, A and B have the same meanings as in formula I, with a corresponding amino-acetonitrile in the presence of a base, such as triethylamine, pyridine or N-ethyl-diisopropylamine, at temperatures between 0° and 100° C., preferably between room temperature and the boiling point of the reaction mixture. The compounds of the formula XVa or XVb needed for this purpose may be prepared by reacting a corresponding azepinone with an alkyl nitrite, such as tert.butylnitrite, in a solvent such as diethyl ether, tetrahydrofuran or dioxane at temperatures between −50° and +25° C. The required azepinones are disclosed in the literature [see A. K. Jokoo et al., Bull Chem. Soc., Japan 29, 631 (1959) and U.S. Pat. No. 3,987,047]. The required tetrahydro-4,5-bis-(trimethylsilyloxy)-azepines may be obtained by acyloin condensation a corresponding dicarboxylic acid diester with sodium in the presence of chloro-trimethylsilane [see J. Org. Chem. 42, 24 (1977) or Synthesis 263 (1971)].

A compound of the formula V may be obtained by reacting a corresponding enamine with an ethyl-O-(p-toluene-sulfonyl)-isonitrosocyanoacetate and then with ammonia. The enamine is obtainable by reacting a corresponding azepinone with morpholine.

A starting compound of the formula VIIIa or VIIIb may, for example, be obtained by halogenating a corresponding azepinone, and reacting the hydrohalide thus obtained with one equivalent each of hydroxylamine hydrochloride and sodium ehtylate, whereby the hydrohalide of a compound of the formula VIIIa or VIIIb is obtained.

A starting compound of the formula XI or XIII is obtained by condensation of a corresponding diketone with a corresponding 2-amino-acetamidine, followed by hydrolysis and/or halogenation, if required.

The following examples illustrate the present invention and will enable others skilled in the art to understand it more completely. It should be understood, however, that the invention is not limited solely to the particular examples given below.

Preparation of starting compounds of the formula IV

EXAMPLE A

7-Ethyl-2-amine-6,7,8,9-tetrahydro-5H-pyrazino[2,3-d]azepine-1-oxide dihydrochloride First 23 gm (0.16 mol) of 1-ethyl-hexahydro-azepin-4-one and then 19.2 ml of tert.butylnitrite were added dropwise to a mixture of 19 gm (0.16 mol) of potassium tert.butylate and 200 ml of absolute tetrahydrofuran at −40° C., and the resulting mixture was allowed to stand overnight at 0° to 10° C. Thereafter, a solution of 20 gm (0.217 mol) of amino-acetonitrile hydrochloride and 30 gm of N-ethyl-diisopropylamine in 280 ml of chloroform was added, and the resulting mixture was refluxed for 4 hours, then filtered, and the filtrate was evaporated The desired compound was isolated from the isomer mixture residue by silicagel chromatography with acetone/concentrated ammonia (95:5). The dihydrochloride was precipitated from ethanol with ethanolic hydrochloric acid.

Yield: 1.5 gm (3.3% of theory).
Melting point: 227° C. (decomp.).
Calculated: C-42.71%; H-6.45%; N-19.92%; Cl-25.22%. Found: C:42.60%; H-6.68%; N-19.63%; Cl-24.60%.

EXAMPLE B

2-Amino-7-benzyl-6,7,8,9-tetrahydro-5H-pyrazino[2,3-d]azepine-1-oxide

This compound was prepared from 1-benzyl-hexhydroazepin-4-one by oximation with tert.butylnitrite and subsequent reaction with amino-acetonitrile analogous to Example A.

Yield: 4.6% of theory.
Melting point: <20° C.
Calculated: Molpeak m/e=270. Found: Molpeak m/e=270.

EXAMPLE C

7-Acetyl-2-amino-6,7,8,9-tetrahydro-5H-pyrazino[2,3-d]azepine-1-oxide

This compound was prepared analogous to Example A from 1-acetyl-hexahydro-azepin-4-one by oximation with tert.butyl nitrite and subsequent reaction with amino-acetronitrile.

Yield: 9.7% of theory.
Melting point: <20° C.
Calculated: Molpeak m/e=222. Found: Molpeak m/e=222.

EXAMPLE D

Ethyl-2-amino-6,7,8,9-tetrahydro-5H-7-pyrazino-[2,3-d]azepinecarboxylate-1-oxide This compound was prepared analogous to Example A from ethyl hexahydro-azepin-4-one-1-carboxylate by oximation with tert.butyl nitrite and subsequent reaction with amino-acetonitrile.

Yield: 11.8% of theory.
Melting point: <20° C.
Calculated: Molpeak m/e=252. Found: Molpeak m/e=252.

Preparation of end products of formula I

EXAMPLE 1

2-Amino-7-ethyl-6,7,8,9-tetrahydro-5H-pyrazino-[2,3-d]azepine and its dihydrochloride by method A 7.5 gm (25 mmols) 1-ethyl-2,3,6,7-tetrahydro-4,5-bis-(trimethylsilyloxy)-azepine were dissolved in 100 ml of absolute dioxane, and the solution was added dropwise to a solution of 4 gm (25 mmols) of bromine in 50 ml of absolute dioxane, while cooling. 8 ml of absolute pyridine were added to the resulting reaction mixture, and the mixture was added dropwise to a solution of 4.8 gm (40 mmols) of 2-amino-acetamidine dihydrochloride in 200 ml of water, while cooling with ice and vigorously stirring. The resulting mixture was stirred for 5 hours at room temperature, concentrated by evaporation, made strongly alkaline with 2N sodium hydroxide and extracted with chloroform. The extracts were dried over sodium sulfate and then evaporated, and the residue was digested with petroleum ether. The oil left behind after decanting the supernatant liquid was dissolved in ethanol, and the dihydrochloride was precipitated from the solution with ethanolic hydrochloric acid.

Yield: 3.70 gm (56% of theory).
Melting point: 236° C. (decomp.).
Calculated: C-45.29%; H-6.84%; N-21.13%; Cl-26.74%. Found: C:45.61%; H-6.96%; N-21.47%; Cl-26.45%.

EXAMPLE 2

2-Amino-7-methyl-6,7,8,9-tetrahydro-5H-pyrazino[2,3-d]azepine dihydrochloride

This compound was prepared analogous to Example 1 from 2,3,6,7-tetrahydro-1-methyl-4,5-bis-(trimethylsilyloxy)-azepine and 2-amino-acetamidine dihydrobromide.

Yield: 45% of theory.
Melting point: 224° C. (decomp.).
Calculated: C-43.04%; H-6.42%; N-22.31%; Cl-28.23%. Found: C-43.51%; H-6.51%; N-21.30%; Cl-27.95%.

EXAMPLE 3

2-Amino-7-benzyl-6,7,8,9-tetrahydro-5H-pyrazino[2,3-d]azepine by method A 70 gm (0.193 mol) of 1-benzyl-2,3,6,7-tetrahydro-4,5-bis-(trimethylsilyloxy)-azepine were dissolved in 900 ml of carbon tetrachloride, and a solution of 28.8 gm (0.18 mol) of bromine in 80 ml of carbon tetrachloride was added dropwise thereto, while cooling and stirring. The resulting mixture was concentrated by evaporation, the residue was taken up in 400 ml of methanol, the solution was admixed with 100 gm of ice, and 41.1 gm (0.175 mol) of 2-amino-acetamidine dihydrobromide were added. Thereafter, 2N sodium hydroxide was slowly added dropwise at 0° to 5° C., and when a constant pH of 5 was reached the mixture was allowed to stand in the refrigerator for 24 hours. Thereafter, the reaction mixture was evaporated, the residue was taken up in water, the solution was filtered, and the filtrate was made alkaline with sodium hydroxide. The precipitated yellowish-brown crystal slurry was suction-filtered, and the filter cake was dried in vacuo.

Yield: 9.1 gm (20.4% of theory).
Melting point: 112° C.

An additional 5.3 gm (11.9% of theory) of the product was obtained from the aqueous filtrate by extraction with methylene chloride and subsequent column chromatographic purification of the extract solution on silicagel with methanol/methylene chloride (3:1) as the mobile phase.

Calculated: C-70.84%; H-7.13%; N-22.03%. Found: C-70.55%; H-7.05%; N-21.98%.

EXAMPLE 4

2-Amino-7-isopropyl-6,7,8,9-tetrahydro-5H-pyrazino-[2,3-d]azepine dihydrochloride This compound was prepared analogous to Example 1 from 2,3,6,7-tetrahydro-1-isopropyl-4,5-bis-(trimethylsilyloxy)azepine and 2-amino-acetamidine dihydrobromide.

Yield: 46% of theory.
Melting point: 222°-224° C.
Calculated: C-47.32%; H-7.22%; N-20.07%; Cl-25.40%. Found: C-47.32%; H-7.65%; N-19.88%; Cl-25.30%.

EXAMPLE 5

2-Amino-7-propyl-6,7,8,9-tetrahydro-5H-pyrazino[2,3-d]azepine

This compound was prepared analogous to Example 1 from 2,3,6,7-tetrahydro-1-propyl-4,5-bis(trimethylsilyloxy)azepine and 2-amino-acetamidine dihydrobromide.

Yield: 20% of theory.
Melting point: 149° C.
Calculated: C-64.03%; H-8.79%; N-27.16%. Found: C-63.80%; H-8.75%; N-27.19%.

EXAMPLE 6

7-Allyl-2-amino-6,7,8,9-tetrahydro-5H-pyrazino[2,3-d]azepine dihydrochloride

This compound was prepared analogous to Example 1 from 1-allyl-2,3,6,7-tetrahydro-4,5-bis(trimethylsilyloxy)azepine and 2-amino-acetamidine dihydrobromide.

Yield: 26% of theory.
Melting point: 272° C. (decomp.).
Calculated: C-47.66%; H-6.55%; N-20.21%; Cl-25.58%. Found: C-47.50%; H-6.39%; N-20.12%; Cl-25.55%.

EXAMPLE 7

2-Amino-7-butyl-6,7,8,9-tetrahydro-5H-pyrazino[2,3-d]azepine

This compound was prepared analogous to Example 3 from 1-butyl-2,3,6,7-tetrahydro-4,5-bis(trimethylsilyloxy)azepine and 2-amino-acetamidine dihydrobromide.

Yield: 11.3 gm (21.4% of theory).

Melting point: 140°–142° C.
Calculated: C-65.42%; H-9.15%; N-25.44%. Found: C-65.23%; H-9.13%; N-25.56%.

EXAMPLE 8

2-Amino-7-isobutyl-6,7,8,9-tetrahydro-5H-pyrazino[2,3-b]azepine dihydrochloride

This compound was prepared analogous to Example 3 from 1-isobutyl-2,3,6,7-tetrahydro-4,5-bis(trimethylsilyloxy)-azepine and 2-amino-acetamidine dihydrobromide.
Yield: 13% of theory.
Melting point: 149°–151° C.
Calculated: C-49.15%; H-7.56%; N-19.11%; Cl-24.18%. Found: C-49.23%; H-7.63%; N-19.12%; Cl-24.00%.

EXAMPLE 9

2-Amino-7-(butyl-2)-6,7,8,9-tetrahydro-5H-pyrazino[2,3-d]azepine

This compound was prepared analogous to Example 3 from 1-(butyl-2)-2,3,6,7-tetrahydro-4,5-bis(trimethylsilyloxy)azepine and 2-amino-acetamidine dihydrobromide.
Yield: 15% of theory.
Melting point: 113° C.
Calculated: C-65.42%; H-9.15%; N-25.43%. Found: C-65.85%; H-8.99%; N-25.64%.

EXAMPLE 10

2-Amino-7-tert.butyl-6,7,8,9-tetrahydro-5H-pyrazino[2,3-d]azepine

This compound was prepared analogous to Example 3 from 1-tert.butyl-2,3,6,7-tetrahydro-4,5-bis(trimethylsilyloxy)azepine and 2-amino-acetaidine dihydrobromide.
Yield: 37% of theory.
Melting point: 128° C.
Calculated: C-65.41%; H-9.14%; N-25.43%. Found: C-65.20%; H-9.18%; N-25.49%.
Melting point of the dihydrochloride: 190° C. (decomp.).

EXAMPLE 11

2-Amino-7-cyclohexyl-6,7,8,9-tetrahydro-5H-pyrazino[2,3-d]azepine

This compound was prepared analogous to Example 1 from 1-cyclohexyl-2,3,6,7-tetrahydro-4,5-bis(trimethylsilyloxy)azepine and 2-amino-acetamidine dihydrobromide.
Yield: 35% of theory.
Melting point: 167° C.
Calculated: C-68.26%; H-9.00%; N-22.74%. Found: C-68.03%; H-9.24%; N-22.24%.

EXAMPLE 12

2-Amino-7-phenyl-6,7,8,9-tetrahydro-5H-pyrazino-[2,3-d]azepine by method A

A mixture of 35 gm (0.1 mol) of 1-phenyl-2,3,6,7-tetrahydro-4,5-bis(trimethylsilyloxy)-azepine and 750 ml of methanol was boiled for 2 hours. Thereafter, 60 gm (0.3 mol) of copper-II-acetate was added, and the mixture was boiled for 60 minutes more. Subsequently, the reaction mixture was filtered, the filtrate was evaporated, and the residue was extracted with boiling cyclohexane. The cyclohexane extract solution was evaporated, and the residue was dissolved in 250 ml of methanol, and the solution was admixed with 500 gm of ice and 20.6 gm (0.08 mol) of 2-amino-acetamidine dihydrobromide. 2N sodium hydroxide was then added dropwise to the mixture until a constant pH of 5 was reached, and the mixture was allowed to stand overnight in the refrigerator, then concentrated by evaporation, and the residue was made alkaline and extracted with methylene chloride. The dried and concentrated extract solution was chromatographed on silicagel with ethyl acetate as the mobile phase.
Yield: 1.7 gm (8.9% of theory).
Melting point: 95°–97° C.
Calculated: C-69.97%; H-6.71%; N-23.22%. Found: C-69.70%; H-6.70%; N-23.05%.

EXAMPLE 13

2-Amino-7-(4-chloro-benzoyl)-6,7,8,9-tetrahydro-5H-pyrazino-[2,3-d]azepine by method A 53 mg (0.2 mol) of a mixture of 1-(4-chloro-benzoyl)-hexahydroazepine-4,5-dione and 1-(4-chloro-benzoyl)-hexhydroazepine-3,4-dione [prepared from 1-(4-chloro-benzoyl)-hexahydroazepine-4-one by selenium dioxide oxidation in dioxane/water] and 47 gm (0.2 mol) of 2-amino-acetamidine dihydrobromide were dissolved in 700 ml of methanol, and 200 ml of 2N sodium hydroxide were added dropwise to the solution at 5° C. The mixture was stirred at room temperature for one hour, then concentrated by evaporation and then, after addition of more sodium hydroxide, extracted with chloroform. The dried extract solution was concentrated by evaporation and chromatographed on silicagel with ethyl acetate/methanol (10:1) as the mobile phase. The crystals obtained thereby were digested with ethyl acetate and suction-filtered.
Yield: 8.8 gm (14.5% of theory).
Melting point: 190°–192° C.
Calculated: C-59.50%; H-4.99%; N-18.51%; Cl-11.71%. Found: C-59.93%; H-4.70%; N-18.41%; Cl-12.23%.

EXAMPLE 14

2-Amino-7-acetyl-6,7,8,9-tetrahydro-5H-pyrazino[2,3-d]azepine

This compound was prepared analogous to Example 13 by reacting a mixture of 1-acetyl-hexhydroazepine-4,5-dione and 1-acetyl-hexhydroazepine-3,4-dione (prepared from 1-acetyl-hexhydroazepine-4-ones by selenium dioxide oxidation in dioxane/water) with 2-amino-acetamidine dihydrobromide.
Yield: 17% of theory.
Melting point: 205° C.
Calculated: C-58.23%; H-6.84%; N-27.17%. Found: C-58.01%; H-6.51%; N-26.88%.

EXAMPLE 15

Ethyl 2-amino-6,7,8,9-tetrahydro-5H-pyrazino[2,3-d]azepine-7-carboxylate

This compound was prepared analogous to Example 13 by reacting a mixture of ethyl hexahydroazepine-3,4-dione-1-carboxylate and ethyl hexahydroazepine-4,5-dione-1-carboxylate (prepared from ethyl hexahydroazepine-4-one-1-carboxylate by selenium dioxide oxidation) with 2-amino-acetamidine dihydrobromide.
Yield: 21% of theory.

The chloroform extract solution was dried and evaporated, and the residue was chromatographically purified on silicagel with methanol as the mobile phase. Subsequently, the hydrochloride was precipitated from ethanol with ethanolic hydrochloric acid.

Yield: 2.4 gm (29% of theory).
Melting point: 244°–247° C.
Calculated: C-65.33%; H-6.58%; N-15.24%; Cl-12.85%. Found: C-65.01%; H-6.42%; N-14.89%; Cl-12.31%.

(b)

2-Amino-7-benzyl-6,7,8,9-tetrahydro-5H-pyrazino[2,3-d]azepine 2.4 gm (0.01 mol) of 7-benzyl-6,7,8,9-tetrahydro-5H-pyrazino[2,3-d]azepine were dissolved in 20 ml of dimethylaniline, 3.9 gm (0.1 mol) of sodium amide were added, and the mixture was heated for four hours at 170° C. Thereafter, the dimethylaniline was distilled off in a high vacuum, the residue was taken up in 4N sodium hydroxide, and the solution was extracted with chloroform. The chloroform extract solution was dried and column-chromatograpically purified on silicagel with methanol/methylene chloride (3:1) as the mobile phase.

Yield: 0.51 gm (20% of theory).
Melting point: 110°–112° C.
Calculated: C-70.84%; H-7.13%; N-22.03%. Found: C-70.31%; H-6.99%; N-21.75%.

EXAMPLE 22

2-Amino-7-cyclopropyl-6,7,8,9-tetrahydro-5H-pyrazino[2,3-d]azepine and its hydrochloride by method A 7.64 gm (47.8 mmols) of bromine were added dropwise to a mixture of 15.1 gm (191.3 mmols) of pyridine and 200 ml of absolute dioxane at room temperature, accompanied by stirring. The resulting solution was added dropwise to a slightly cooled mixture of 15 gm (47.8 mmols) of 1-cyclopropyl-2,3,6,7-tetrahydro-4,5-bis(trimethylsilyloxy)azepine and 200 ml of absolute dioxane. The resulting mixture was rapidly added dropwise to an ice-cooled solution of 7.0 gm (47.8 mmols) of α-amino-acetamidinedihydrochloride in 200 ml of water, the mixture was stirred for 3 hours and then evaporated in vacuo, and the residue was made alkaline with 2N sodium hydroxide and extraced with chloroform. The chloroform extract solution was dried over magnesium sulfate and evaporated, and the crystalline residue was recrystallized from acetonitrile. The crystalline base thus obtained was dissolved in ethanol and precipitated as the hydrochloride with ethanolic hydrochloric acid.

Yield: 7.45 gm (67.7% of theory).
Melting point: 230° C. (decomp.).
Calculated: C-54.88%; H-7.12%; N-23.27%; Cl-14.72%. Found: C-54.63%; H-6.96%; N-23.10%; Cl-14.85%.

EXAMPLE 23

2-Amino-7-cyclobutyl-6,7,8,9-tetrahydro-5H-pyrazino[2,3-d]azepine dihydrochloride This compound was prepared analogous to Example 22 from 1-cyclobutyl-2,3,6,7-tetrahydro-4,5-bis(trimethylsilyloxy)-azepine and α-amino-acetamidine dihydrochloride.

Yield: 51% of theory.
Melting point: 265°–270° C. (decomp.).
Calculated: C-49.49%; H-6.92%; N-19.24%; Cl-24.35%. Found: C-49.95%; H-7.15%; N-19.18%; Cl-24.40%.

EXAMPLE 24

2-Amino-7-(β-phenethyl)-6,7,8,9-tetrahydro-5H-pyrazino[2,3-d]azepine dihydrochloride This compound was prepared analogous to Example 22 from 1-(β-phenethyl)-2,3,6,7-tetrahydro-4,5-bis(trimethylsilyloxy)-azepine and α-amino-acetamidine dihydrochloride.

Yield: 53% of theory.
Melting point: 216°–220° C. (decomp.).
Calculated: C-56.31%; H-6.50%; N-16.42%; Cl-20.78%. Found: C-56.76%; H-6.74%; N-16.74%; Cl-20.58%.

EXAMPLE 25

2-Amino-7-(3-phenyl-propyl)-6,7,8,9-tetrahydro-5H-pyrazino[2,3-d]azepine dihydrochloride This compound was prepared analogous to Example 22 from 1-(3-phenyl-propyl)-2,3,6,7-tetrahydro-4,5-bis(trimethylsilyloxy)-azepine and α-amino-acetamidine dihydrochloride.

Yield: 39.5% of theory.
Melting point: 228°–230° C. (decomp.).
Calculated: C-57.48%; H-6.81%; N-15.77%; Cl-19.96%. Found: C-58.10%; H-6.83%; N-15.86%; Cl-19.90%.

EXAMPLE 26

2-Amino-5(R,S),7,9(R,S)-trimethyl-6,7,8,9-tetrahydro-5H-pyrazino[2,3-d]azepine dihydrochloride This compound was prepared analogous to Example 22 from 1,3(R,S),6(R,S)-trimethyl-2,3,6,7-tetrahydro-4,5-bis-(trimethylsilyloxy)-azepine and α-amino-azetamidine dihydrochloride.

Yield: 20% of theory.
Melting point: 240°–242° C. (decomp.).
Calculated: C-47.32%; H-7.22%; N-20.07%. Found: C-47.76%; H-7.47%; N-19.75%.

EXAMPLE 27

2-Amino-7-ethyl-6,7,8,9-tetrahydro-5(R,S)-methyl-5H-pyrazino[2,3-d]azepine dihydrochloride and 3-amino-7-ethyl-6,7,8,9-tetrahydro-5(R,S)-methyl-5H-pyrazino[2,3-d]azepine dihydrochloride These isomeric compounds were prepared analogous to Example 22 from 1-ethyl-2,3,6,7-tetrahydro-3(R,S)-methyl-4,5-bis(trimethylsilyloxy)-azepine and α-amino-acetamidine dihydrochloride.

Yield: 17,5% of theory.
Melting point: 219°–220° C. (decomp.).
Calculated: C-47.32%; H-7.22%; N-20.07%. Found: C-47.80%; H-7.29%; N-19.80%.

EXAMPLE 28

2-Amino-6,7,8,9-tetrahydro-5H-pyrazino[2,3-d]-azepine dihydrobromide 11.5 gm (45 mmols) of 2-amino-7-benzyl-6,7,8,9-tetrahydro-5H-pyrazino[2,3-d]azepine and 11.6 gm (90 mmols) of N-ethyl-diisopropylamine were dissolved in 100 ml of methylene chloride, and the solution was admixed dropwise with 15.4 gm (90 mmols) of benzyl chloroformate. The mixture was stirred for 48 hours Melting point: 135° C.
Calculated: C-55.91%; H-6.89%; N-23.71%. Found: C-56.18%; H-6.87%; N-23.40%.

EXAMPLE 16

2-Amino-6,7,8,9-tetrahydro-5H-pyrazino[2,3-d]azepine 11.15 gm (47.2 mmols) of ethyl 2-amino-6,7,8,9-tetrahydro-5H-pyrazino[2,3-d]azepine-7-carboxylate were dissolved in 300 ml of ethanol, and the solution was admixed with 30 gm of potassium hydroxide. The mixture was evaporated to dryness, and the residue was heated for 3 hours at 100° C. and then taken up in water. The aqueous solution was extracted with chloroform with the aid of a heavy phase perforator, and the chloroform extract solution was purified on a silicagel column with chloroform/methanol/concentrated ammonia (24:12:1) as the mobile phase.

Yield: 3.6 gm (46% of theory).
Melting point: 138°–140° C.
Calculated: C-58.51%; H-7.37%; N-34.11%. Found: C-58.68%; H-7.28%; N-33.95%.

EXAMPLE 17

2-Amino-7-(4-chloro-benzyl)-6,7,8,9-tetrahydro-5H-pyrazino[2,3-d]azepine 3.7 gm (12.2 mmols) of 2-amino-7-(4-chloro-benzoyl)-6,7,8,9-tetrahydro-5H-pyrazino[2,3-d]-azepine were dissolved in 50 ml of absolute tetrahydrofuran, and the solution was added dropwise to a suspension of 2.8 gm (73.3 mmols) of lithium aluminum hydride in tetrahydrofuran. The mixture was stirred for 3 hours at room temperature, and then the excess lithium aluminum hydride was decomposed with 2N sodium hydroxide and the precipitated aluminate was filtered off. The filtrate was concentrated by evaporation and chromatographed on silicagel with ethyl acetate/methanol (5:1) as the mobile phase. Thereafter, the product was dissolved in absolute ether, and the solution was evaporated until crystallization commenced.

Yield: 1.5 gm (43% of theory).
Melting point: 158° C.
Calculated: C-62.38%; H-5.94%; N-19.41%. Found: C-62.67%; H-6.10%; N-18.94%.

EXAMPLE 18

2-Amino-7-ethyl-6,7,8,9-tetrahydro-5H-pyrazino[2,3-d]azepine monohydrochloride

This compound was prepared analogous to Example 17 from 7-acetyl-2-amino-6,7,8,9-tetrahydro-5H-pyrazino[2,3-d]azepine by reduction with lithium aluminum hydride and subsequent precipitation of the monohydrochloride.

Yield: 28% of theory.
Melting point: 247°–251° C. (decomp.).
Calculated: C-52.51%; H-7.49%; N-24.50%; Cl-15.50%. Found: C-52.61%; H-7.67%; N-24.30%; Cl-15.15%.

EXAMPLE 19

2-Amino-7-ethyl-6,7,8,9-tetrahydro-5H-pyrazino[2,3-d]azepine dihydrochloride by method B 1.04 gm (5 mmols) of 2-amino-7-ethyl-6,7,8,9-tetrahydro-5H-pyrazino[2,3-d]azepine-1-dioxide were dissolved in a mixture of 15 ml water and 15 ml ethanol, 2 gm of sodium dithionite were added to the solution, and the mixture was refluxed for 30 hours, an additional 0.5 gm of sodium dithionite, 5 ml of water and 5 ml of ethanol being added each hour. Thereafter, the reaction mixture was concentrated by evaporation, and the residue was made alkaline and extracted with chloroform. After chromatography of the product on silicagel, the dihydrochloride was precipitated from ethanol with ethanolic hydrochloric acid.

Yield: 0.45 gm (34% of theory).
Melting point: 233° C. (decomp.).

EXAMPLE 20

2-Amino-6,7,8,9-tetrahydro-5H-pyrazino[2,3-d]azepine by method C (a) Diethyl 2-amino-6,7,8,9-tetrahydro-5H-pyrazino[2,3-d]azepine-3,7-dicarboxylate 25.4 gm (0.1 mol) of an isomer mixture of ethyl 4-morpholino-2,5,6,7-tetrahydro-1H-azepine-1-carboxylate and ethyl 4-morpholino-2,3,6,7-tetrahydro-1H-azepine-1-carboxylate were added dropwise to a solution of 14.8 gm (50 mmols) of ethyl O-(p-toluenesulfonyl)-isonitrosocyanoacetate in 250 ml of absolute ether at room temperature, and the mixture was allowed to stand overnight. Thereafter, the mixture was evaporated, the residue was taken up in methylene chloride, and the resulting solution was washed with water, dried over sodium sulfate and evaporated. The residue was admixed with 300 ml of a saturated ethanolic solution of ammonia, and the mixture was allowed to stand at room temperature for 24 hours. Thereafter, the mixture was evaporated, and the residue was chromatographed on silicagel with ethyl acetate as the mobile phase. The product thus obtained was digested with a little ether, suction-filtered and recrystallized from acetonitrile.

Yield: 1.6 gm (10% of theory).
Melting point: 166°–168° C.
Calculated: C-54.53%; H-6.54%; N-18.17%. Found: C-54.69%; H-6.43%; N-18.55%.

(b) 2-Amino-6,7,8,9-tetrahydro-5H-pyrazino[2,3-d]azepine

A mixture of 1.6 gm (5.2 mmols) of diethyl 2-amino-6,7,8,9-tetrahydro-5H-pyrazino[2,3-d]azepine-3,7-dicarboxylate and 20 ml of 80% sulfuric acid was heated for 30 minutes at 180° C. Thereafter, the mixture was cooled, made alkaline with an aqueous sodium carbonate solution, and extracted with chloroform for 24 hours with a perforator. The chloroform extract was chromatographed in silicagel with chloroform/methanol/concentrated ammonia (24:12:1) as the mobile phase.

Yield: 0.1 gm (11.7% of theory).
Melting point: 137°–139° C.

EXAMPLE 21

2-Amino-7-benzyl-6,7,8,9-tetrahydro-5H-pyrazino-[2,3-d]azepine by method A (a) 7-Benzyl-6,7,8,9-tetrahydro-5H-pyrazino[2,3-d]azepine hydrochloride 10.9 gm (30 mmols) of 1-benzyl-2,3,6,7-tetrahydro-4,5-bis(trimethylsilyloxy)-azepine were dissolved in a mixture of 20 ml ethylenediamine and 30 ml tetraethyleneglycol dimethyl ether, and air was passed through the solution at 120° C. for eight hours. Thereafter, the reaction mixture was poured into water, and the aqueous composition was extracted with chloroform.

and then evaporated in vacuo, and the residue was dissolved in a mixture of 50 ml glacial acetic acid and 50 ml glacial acetic acid saturated with hydrobromic acid. The resulting solution was heated for 2 hours at 100° C. and then evaporated, the residue was triturated with glacial acetic acid, the crystalline slurry formed thereby was suction-filtered, and the filter cake was washed with ethyl acetate.

Yield: 13.8 gm (94% of theory).
Melting point: 240°–243° C.

EXAMPLE 29

2-Amino-7-(p-chlorophenyl-acetyl)-6,7,8,9-tetrahydro-5H-pyrazino[2,3-d]azepine by method F 5.8 gm (17.9 mmols) of 2-amino-6,7,8,9-tetrahydro-5H-pyrazino[2,3-d]azepine dihydrobromide were dissolved in 50 ml of 2N hydroxide, and the solution was admixed dropwise with an ice-cooled solution of 7.5 gm of p-chlorophenyl-acetyl chloride in 50 ml of dioxane. The resulting mixture was stirred overnight and then evaporated, and the residue was extracted with chloroform. The chloroform extract was dried and then evaporated, and the residue was triturated with carbon tetrachloride and suction-filtered.

Yield: 3.6 gm (63% of theory).
Melting point: 183°–187° C.
Calculated: C-60.66%; H-5.41%; N-17.68%; Cl-11.19%. Found: C-60.29%; H-5.20%; N-17.54%; Cl-11.01%.

EXAMPLE 30

2-Amino-7-(p-chloro-benzoyl)-6,7,8,9-tetrahydro-5H-pyrazino[2,3-d]azepine

This compound was prepared analogous to Example 29 from 2-amino-6,7,8,9-tetrahydro-5H-pyrazino[2,3-d]azepine dihydrobromide and p-chloro-benzoyl chloride.

Yield: 82.5% of theory.
Melting point: 189°–191° C.
Calculated: C-59.50%; H-4.99%; N-18.51%; Cl-11.71%. Found: C-59.53%; H-4.71%; N-18.41%; Cl-11.93%.

EXAMPLE 31

2-Amino-7-(p-chloro-benzyl)-6,7,8,9-tetrahydro-5H-pyrazino[2,3-d]azepine 3.0 gm (9.2 mmols) of 2-amino-6,7,8,9-tetrahydro-5H-pyrazino[2,3-d]azepine dihydrobromide were suspended in 100 ml of acetonitrile, 7.5 ml of N-ethyl-diisopropylamine were added to the suspension, and the mixture was admixed dropwise with 1.5 gm (9.3 mmols) of p-chloro-benzyl-chloride. The reaction mixture was stirred for 48 hours and then evaporated, the residue was acidified with dilute hydrochloric acid, and the mixture was extracted with methylene chloride. The aqueous phase was made alkaline and then exhaustively extracted with methylene chloride, the extracts were evaporated, and the residue was column-chromatographically purified on silicagel with ethyl acetate as the mobile phase.

Yield: 480 mgm (18.7% of theory).
Melting point: 158°–160° C.
Calculated: C-62.39%; H-5.93%; N-19.40%; Cl-12.28%. Found: C-62.70%; H-6.10%; N-19.33%; Cl-12.37%.

EXAMPLE 32

2-Amino-7-[β-(p-chloro-phenyl)-ethyl]-6,7,8,9-tetrahydro-5H-pyrazino[2,3-d]azepine dihydrochloride 3 gm (9.5 mmols) of 2-amino-7-(p-chlorophenylacetyl)-6,7,8,9-tetrahydro-5H-pyrazino[2,3-d]azepine were added in portions to a stirred suspension of 3.8 gm (0.1 mol) of lithium aluminum hydride in 150 ml of absolute tetrahydrofuran, and the mixture was stirred overnight. Thereafter, the excess lithium aluminum hydride was decomposed with 2N sodium hydroxide, the precipitated sodium aluminate was suction-filtered off, and the filtrate was evaporated. The residue was column-chromatographically purified on silicagel with ethyl acetate/methanol (2:1) as the mobile phase, and the dihydrochloride was precipitated with ethanolic hydrochloric acid.

Yield: 0.5 gm (14% of theory).
Melting point: 175°–180° C.
Calculated: C-51.15%; H-5.63%; N-14.91%; Cl-28.31%. Found: C-51.54%; H-5.94%; N-14.51%; Cl-27.98%.

EXAMPLE 33

2-Amino-7-ethyl-6,7,8,9-tetrahydro-3-methyl-5H-pyrazino[2,3-d]azepine dihydrochloride This compound was prepared analogous to Example 22 from 1-ethyl-2,3,6,7-tetrahydro-4,5-bis(trimethylsilyloxy)azepine and α-amino-propionamidine.

Yield: 48% of theory.
Melting point: 263° C. (decomp.).
Calculated: C-47.32%; H-7.22%; N-20.07%; Cl-25.40%. Found: C-47.19%; H-7.48%; N-19.81%; Cl-24.90%.

EXAMPLE 34

2-Amino-3,7-diethyl-6,7,8,9-tetrahydro-5H-pyrazino[2,3-d]azepine dihydrochloride This compound was prepared analogous to Example 22 from 1-ethyl-2,3,6,7-tetrahydro-4,5-bis(trimethylsilyloxy)azepine and α-amino-butyramidine dihydrobromide.

Yield: 46.5% of theory.
Melting point: 247° C. (decomp.).
Calculated: C-49.15%; H-7.56%; N-19.11%; Cl-24.18%. Found: C-49.35%; H-7.64%; N-18.90%; Cl-24.38%.

EXAMPLE 35

2-Amino-7-ethyl-6,7,8,9-tetrahydro-3-phenyl-5H-pyrazino[2,3-d]azepine dihydrochloride This compound was prepared analogous to Example 22 from 1-ethyl-2,3,6,7-tetrahydro-4,5-bis(trimethylsilyloxy)azepine and α-phenyl-α-amino-acetamidine dihydrobromide.

Yield: 54% of theory.
Melting point: 245°–247° C. (decomp.).
Calculated: C-56.31%; H-6.50%; N-16.42%; Cl-20.78%. Found: C-56.30%; H-6.71%; N-16.26%; Cl-20.42%.

EXAMPLE 36

Ethyl 2-amino-7-ethyl-6,7,8,9-tetrahydro-5H-pyrazino[2,3-d]azepine-3-carboxylate dihydrochloride This compound was prepared analogous to Example 22 from 1-ethyl-2,3,6,7-tetrahydro-4,5-bis(trimethylsilyloxy)azepine and ethyl 2-amidino-2-aminoacetate dihydrochloride.

Yield: 17.5% of theory.
Melting point: 217° C.
Calculated: C-46.30%; H-6.58%; N-16.61%; Cl-21.03%. Found: C-46.35%; H-6.65%; N-16.85%; Cl-21.05%.

EXAMPLE 37

2-Amino-3-chloro-7-ethyl-6,7,8,9-tetrahydro-5H-pyrazino[2,3-d]azepine hydrochloride 6 gm (31.3 mmols) of 2-amino-7-ethyl-6,7,8,9-tetrahydro-5H-pyrazino[2,3-d]azepine were dissolved in 100 ml of glacial acetic acid and, while cooling the solution with ice, chlorine was introduced until the thin-layer chromatogram showed that no more starting material was present. Thereafter, the reaction mixture was made alkaline with 2N sodium hydroxide and was then extracted with chloroform. The chloroform extract solution was evaporated, and the residue was column-chromatographically purified on silicagel with ethyl acetate/methanol/ethanolic ammonia (4:1:0.5) as the mobile phase. The hydrochloride was precipitated from ethanol with ethanolic hydrochloric acid.

Yield: 1.8 gm (21.8% of theory).
Melting point: 306° C. (decomp.).
Calculated: C-45.64%; H-6.13%; N-21.29%; Cl-26.94%. Found: C-45.80%; H-6.11%; N-21.22%; Cl-27.10%.

EXAMPLE 38

2-Amino-3-bromo-7-ethyl-6,7,8,9-tetrahydro-5H-pyrazino[2,3-d]azepine hydrochloride This compound was prepared analogous to Example 37 from 2-amino-7-ethyl-6,7,8,9-tetrahydro-5H-pyrazino[2,3-d]azepine and bromine.

Yield: 64.5% of theory.
Melting point: 312° C. (decomp.).
Calculated: C-39.04%; H-5.24%; N-18.21%; Cl-11.52%; Br-25.97%. Found: C-38.81%; H-5.06%; N-18.65%; Cl-11.65%; Br-26.20%.

EXAMPLE 39

2-Amino-3-methyl-7-ethyl-6,7,8,9-tetrahydro-5H-pyrazino[2,3-d]azepine dihydrochloride by method G 1 gm (3.3 mmols) of 2-amino-3-bromo-7-ethyl-6,7,8,9-tetrahydro-5H-pyrazino[2,3-d]azepine hydrochloride were admixed with a solution of 1 gm (43.5 mmols) of sodium in 50 ml of methanol, and the mixture was stirred for 10 hours at 150° C. in an autoclave. Thereafter, the reaction mixture was evaporated, the residue was taken up in 2N sodium hydroxide, and the solution was extracted with chloroform. The chloroform extract solution was evaporated, the residue was dissolved in acetone, and the solution was admixed with ethanolic hydrochloric acid, yielding the hydrochloride in the form of white crystals.

Yield: 150 mgm (15.4% of theory).
Melting point: Beginning at 150° C., clear at 245° C.

Calculated: C-44.75%; H-6.83%; N-18.98%; Cl-24.02%. Found: C-44.65%; H-6.85%; N-19.00%; Cl-24.05%.

EXAMPLE 40

2-Amino-7-benzyl-6,7,8,9-tetrahydro-5H-pyrazino[2,3-d]azepine by method E 24 gm (66 mmols) of 1-benzyl-5-bromo-hexhydroazepin-4-one hydrobromide (prepared by bromination of 1-benzyl-hexahydro-azepin-4-one with bromine in glacial acetic acid) were dissolved in ethanol, 4.6 gm (66 mmols) of hydroxylamine hydrochloride were added to the solution, and the mixture was admixed dropwise with a solution of 1.5 gm (65.2 mmols) of sodium in 20 ml of ethanol. The mixture was stirred overnight at 30°–40° C., then filtered, and the filtrate was evaporated. 6.1 gm (66 mmols) of α-amino-acetonitrile hydrochloride and 100 ml of chloroform were added and, while stirring, 27.7 ml (0,2 mol) of triethylamine were added dropwise, and the resulting mixture was stirred overnight. Thereafter, the reaction mixture was evaporated, the residue was admixed with 2N sodium hydroxide, and the mixture was extracted with chloroform. The extract solution was dried and evaporated, and the residue was first column-chromatographically purified on silicagel with toluene/ethyl acetate (2:1) as the mobile phase and then recrystallized from carbon tetrachloride.

Yield: 2.5 gm (15% of theory).
Melting point: 115°–118° C.
Calculated: C-70.84%; H-7.13%; N-22.03%. Found: C-70.64%; H-7.13%; N-22.03%.

EXAMPLE 41

2-Amino-7-ethyl-6,7,8,9-tetrahydro-5H-pyrazino[2,3-d]azepine

This compound was prepared analogous to Example 40 from 1-ethyl-5-bromo-hexahydro-azepin-4-one hydrobromide, hydroxylamine and α-amino-acetonitrile hydrochloride.

Yield: 6% of theory.
Melting point: 83°–84° C.
Calculated: C-62.47%; H-8.39%; N-29.14%. Found: C-62.31%; H-8.07%; N-28.95%.

EXAMPLE 42

2-Amino-7-ethyl-6,7,8,9-tetrahydro-6(R,S)-methyl-5H-pyrazino[2,3-d]azepine dihydrochloride and 3-amino-7-ethyl-6,7,8,9-tetrahydro-6(R,S)-methyl-5H-pyrazino[2,3-d]azepine dihydrochloride These isomeric compounds were prepared analogous to Example 22 from 1-ethyl-2,3,6,7-tetrahydro-2(R,S)-methyl-4,5-bis(trimethylsilyloxy)-azepine and α-aminoacetamidine dihydrochloride.

Yield: 11% of theory.
Melting point: above 200° C.
Calculated: C-47.32%; H-7.22%; N-20.06%. Found: C-47.21%; H-7.01%; N-19.56%.

EXAMPLE 43

2-Amino-7-ethyl-6,7,8,9-tetrahydro-5H-pyrazino[2,3-d]azepine

This compound was prepared analogous to Example 31 by alkylation of 2-amino-6,7,8,9-tetrahydro-5H-pyrazino[2,3-d]azepine dihydrobromide with ethyl bromide.

Yield: 34% of theory.
Melting point: 84°–85° C.
Calculated: Molpeak m/e=192. Found: Molpeak m/e=192.

EXAMPLE 44

2-Amino-6-ethyl-5,6,7,8-tetrahydro-pyrido[3,4-b]pyrazine dihydrochloride

This compound was prepared analogous to Example 22 from 1-ethyl-1,2,5,6-tetrahydro-3,4-bis(trimethylsilyloxy)pyridine and α-amino-acetamidine dihydrochloride.

Yield: 14% of theory.
Melting point: 255°–258° C.
Calculated: C-43.04%; H-6.42%; N-22.31%; Cl-28.23%. Found: C-43.35%; H-6.64%; N-22.53%; Cl-27.80%.

EXAMPLE 45

3-Amino-6-ethyl-5,6,7,8-tetrahydro-pyrido[3,4-b]pyrazine dihydrochloride (a)
3-Amino-6-acetyl-5,6,7,8-tetrahydro-pyrido[3,4-b]pyrazine-4-oxide This starting compound was prepared analogous to Example A from 1-acetyl-piperidin-4-one and tert. butyl nitrite.

Melting point: 235°–237° C. (decomp.).

(b)
3-Amino-6-acetyl-5,6,7,8-tetrahydro-pyrido[3,4-b]pyrazine

This intermediate was prepared analogous to Example 19 from 3-amino-6-acetyl-5,6,7,8-tetrahydro-pyrido[3,4-b]pyrazine-4-oxide by reduction with sodium dithionite.

Yield: 46.9% of theory.
Melting point: 183°–185° C.
Calculated: C-56.24%; H-6.29%; N-29.15%. Found: C-56.12%; H-6.14%; N-28.52%.

(c)
3-Amino-6-ethyl-5,6,7,8-tetrahydro-pyrido[3,4-b]pyrazine dihydrochloride

This compound was prepared analogous to Example 17 from 3-amino-6-acetyl-5,6,7,8-tetrahydro-pyrido[3,4-b]pyrazine by reduction with lithium aluminum hydride.

Yield: 14.3% of theory.
Melting point: 249°–251° C. (decomp.).
Calculated: C-43.04%; H-6.42%; N-22.31%; Cl-28.23%. Found: C-43.41%; H-6.57%; N-22.10%; Cl-28.02%.

EXAMPLE 46

2-Amino-5,6,7,8-tetrahydro-6-methyl-pyrido[3,4-b]pyrazine dihydrochloride and
3-amino-5,6,7,8-tetrahydro-6-methylpyrido[3,4-b]pyrazine dihydrochloride These isomeric compounds were prepared analogous to Example 22 from 1-methyl-1,2,5,6-tetrahydro-3,4-bis-(trimethylsilyloxy)-pyridine and α-amino-acetamidine dihydrochloride.

Yield: 9.1% of theory.
Melting point: 220°–225° C.

Calculated: C-40.51%; H-5.95%; N-23.62%. Found: C-41.25%; H-6.25%; N-23.60%.

EXAMPLE 47

2-Amino-5,6,7,8-tetrahydro-6-propyl-pyrido[3,4-b]pyrazine dihydrochloride and
3-amino-5,6,7,8-tetrahydro-6-propylpyrido[3,4-b]pyrazine dihydrochloride These isomeric compounds were obtained analogous to Example 22 from 1-propyl-1,2,5,6-tetrahydro-3,4-bis(trimethylsilyloxy)-pyridine and α-amino-acetamidine dihydrochloride.

Yield: 8.5% of theory.
Melting point: 222° C.
Calculated: C-45.29%; H-6.84%; N-21.13%. Found: C-45.80%; H-6.49%; N-20.90%.

EXAMPLE 48

2-Amino-5,6,7,8-tetrahydro-6-isopropyl-pyrido[3,4-b]pyrazine dihydrochloride and
3-amino-5,6,7,8-tetrahydro-6-isopropyl-pyrido[3,4-b]-pyrazine dihydrochloride These isomeric compounds were obtained analogous to Example 22 from 1-isopropyl-1,2,5,6-tetrahydro-3,4-bis-(trimethylsilyloxy)-pyridine and α-amino-acetamidine dihydrochloride.

Yield: 10.2% of theory.
Melting point: 215°–220° C.
Calculated: C-45.29%; H-6.84%; N-21.13%; Cl-26.74%. Found: C-45.27%; H-6.91%; N-21.22%; Cl-26.35%.

EXAMPLE 49

2-Amino-6-benzyl-5,6,7,8-tetrahydro-pyrido[3,4-b]pyrazine dihydrochloride and
3-amino-6-benzyl-5,6,7,8-tetrahydropyrido[3,4-b]-pyrazine dihydrochloride These compounds were prepared from 1-benzyl-1,2,5,6-tetrahydro-3,4-bis(trimethylsilyloxy)-pyridine and α-amino-acetamidine dihydrochloride analogous to Example 22.

Yield: 19% of theory.
Melting point: 261° C. (decomp.).
Calculated: C-53.68%; H-5.79%; N-17.89%; Cl-22.64%. Found: C-54.05%; H-5.76%; N-18.07%; Cl-22.40%.

EXAMPLE 50

2-Amino-7-isopropyl-6,7,8,9-tetrahydro-5H-pyrazino[2,3-d]azepine dihydrochloride by method F 1,64 gm (10 mmols) of 2-amino-6,7,8,9-tetrahydro-5H-pyrazino[2,3-d]azepine were dissolved in 100 ml of isopropanol, 16 gm of Raney nickel were added to the solution, and the mixture was refluxed for 6 hours. Thereafter, the Raney nickel was filtered off, the filtrate was evaporated, and the residue was purified by chromatography on silicagel with methanol/methylene chloride (3:1) as the mobile phase. The dihydrochloride was precipitated from a solution of the purified product in ethanol with ethanolic hydrochloric acid and collected by suction filtration.

Yield: 1.5 gm (53.7% of theory).
Melting point: 221°–223° C.

EXAMPLE 50a

6-Ethyl-2-amino-6,7-dihydro-5H-pyrrolo[3,4-b]pyrazine

This compound was prepared analogous to Example 22 from 1-ethyl-2,5-dihydro-3,4-bis(trimethylsilyloxy)-pyrrole and α-amino-acetamidine dihydrochloride.

Yield: 7% of theory.

Melting point: <20° C.

Calculated: Molpeak m/e=164. Found: Molpeak m/e=164.

The compounds of the present invention, that is, those embraced by formula I above and their non-toxic acid addition salts, have useful pharmacodynamic properties. More particularly, they exhibit bradycardiac activities in warm-blooded animals such as rats.

The bradycardiac property, the effect upon blood pressure and the toxicity of the compounds of this invention were ascertained by the test methods described below, and the results of these tests for a few representative species of the genus are shown in the tables, where A=7-Ethyl-2-amino-6,7,8,9-tetrahydro-5H-pyrazino[2,3-d]azepine dihydrochloride, B=7-Allyl-2-amino-6,7,8,9-tetrahydro-5H-pyrazino[2,3-d]azepine dihydrochloride, C=2-Amino-6,7,8,9-tetrahydro-7-methyl-5H-pyrazino[2,3-d]azepine dihydrochloride, D=7-Ethyl-2-amino-3-bromo-6,7,8,9-tetrahydro-5H-pyrazino[2,3-d]azepine hydrochloride, E=7-Ethyl-2-amino-3-chloro-6,7,8,9-tetrahydro-5H-pyrazino[2,3-d]azepine hydrochloride, F=7-Ethyl-2-amino-6,7,8,9-tetrahydro-3-methyl-5H-pyrazino-[2,3-d]azepine dihydrochloride, G=6-Ethyl-2-amino-5,6,7,8-tetrahydro-pyrido[3,4-b]pyrazine dihydrochloride, and H=2-Amino-7-cyclopropyl-6,7,8,9-tetrahydro-5H-pyrazino[2,3-d]azepine hydrochloride.

1. Effect upon blood pressure and heart rate

Method:

The changes in the circulation of intact, anesthetized rats after intravenous injection of the test compound were recorded.

Description of test:

Male laboratory rats having a body weight of 120–360 gm were anesthetized with pentobarbital (70 mgm/kg). The animals breathed spontaneously through a tracheal cannula. The blood pressure was continuously measured in an *A. carotis* with the aid of an electro-mechanical pressure transducer; the pulse wave triggered a tachograph which continuously recorded the heart rate. Both parameters were plotted on a polygraph. The test compound was injected through a catheter into a V. jugularis.

At a dose of 3 mgm/kg i.v. the test compounds produced an initial increase in the blood pressure of short duration and then a long-lasting decrease in the blood pressure. The decrease in the heart rate was distinct and of long duration.

The following table shows the maximum values which were obtained:

TABLE I

| Compound | Dose mg/kg i.v. | Blood pressure in mm Hg pressor phase | depressor phase | Heart rate reduction beats/minute |
|---|---|---|---|---|
| A | 3 | +61 | −20 | −116 |
| B | 3 | +40 | −20 | −122 |
| C | 3 | +26 | −36 | −105 |
| D | 3 | +50 | −5 | −55 |
| E | 3 | +32 | −11 | −70 |
| F | 3 | +38 | −10 | −78 |
| G | 3 | +6 | −41 | −145 |
| H | 3 | +51 | −28 | −110 |

2. Effect on presynaptic α-adrenoceptors: Inhibition of electrically induced tachycardia Method:

There is an auto-regulation system of the noradrenaline release at the adrenergic nerve ends. The stimulation of presynaptic α-adrenoreceptors has an inhibiting effect upon the noradrenaline release and thus a limiting effect upon the adrenergic neurotransmission. Accordingly, upon stimulation of these "feedback receptors", the effect of a given adrenergic stimulation on the sense organ is reduced.

In the model of the electrically stimulated spinal rat, a tachycardia which is electrically induced at the heart is reduced by presynaptic α-mimetic acting substances.

Description of test:

Male laboratory rats having a body weight of 350–400 gm were anesthetized with pentobarbital (50 mgm/kg i.p.), vagotomized, treated with atropine (1 mgm/kg s.c.), and a tracheal cannula was inserted. After enucleation of an eye, the orbita was punctured, the brain was destroyed, and a metal rod was pushed through the vertebral canal. Artificial respiration was applied to the animals, and they were pre-treated with gallamine (4 mgm/kg i.v.). The metal rod which was used had a diameter of 2.5 mm and, with the exception of a section between the 7th and 8th cm measured from the tip, was insulated with baked-on enamel. Upon insertion of the rod into the vertebral canal, this uninsulated section is positioned in the area of the last cervical vertebra and the first thoracic vertebra. With the aid of a stimulator a supramaximal stimulus (rectangular impulses 50 V, 2 ms; 0.2 Hz; duration of stimulus 25 sec.) was applied against a counter-electrode inserted into the neck skin.

The blood pressure was measured in an *A. carotis* by means of an electro-mechanical pressure transducer. The pulse wave triggered a tachograph which continuously displayed the heart rate. Both of these signals were recorded on a polygraph.

From the raw data thus obtained, the dose of the test compound which inhibits the electrically induced tachycardia by 50% ($D_{50}$) was determined.

The following table shows the results which were obtained:

TABLE II

| Compound | $D_{50}$ |
|---|---|
| A | 28 μgm/kg i.v. |
| G | 670 μgm/kg i.v. |

3. Effect on postsynaptic α-adrenoreceptos: Hypertensive activity in the spinal rat Method:

The increase in blood pressure which occurs upon stimulation of postsynaptic α-adrenoreceptos was measured on the spinal rat model.

Description of test:

Male laboratory rats having a body weight of 200–250 gm were anesthetized (1.2 gm/kg urethane i.p., 1 mgm/kg atropine s/c/). Thereafter, the central spinal cord canal was opened, the spinal cord was severed at $C_1$, and the medulla oblongata and the brain were destroyed with a metal sound. Artificial respiration was applied to the animals, and a polyethylene catheter was tied into a jugular vein. The blood pressure was measured in an *A. carotis* and continuously recorded by means of a Statham element on a Grass polygraph. The test compound was administered i.v. by way of the catheter.

From the raw data thus obtained, the dose of the test compound which increases the arterial blood pressure by 30 mm Hg ($D_{30}$) was determined.

The following table shows the results which were obtained.

TABLE III

| Compound | $D_{30}$ |
|---|---|
| A | 480 μgm/kg i.v. |
| B | 2.6 mgm/kg i.v. |
| G | 1.4 mgm/kg i.v. |

4. Acute toxicity

The acute toxicity was determined in mice after oral or intravenous administration. Observation time: 14 days.

The following table shows the results which were obtained:

TABLE IV

| Compound | $LD_{50}$ |
|---|---|
| A | 215 mgm/kg i.v. |
| | 1,250 mgm/kg p.o. |

By virtues of the above pharmacological properties the compounds of the present invention are useful for the treatment of cardiac and circulatory diseases and pectanginous disorders, and for lowering the heart rate.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.003 to 0.14 mgm/kg body weight, preferably 0.003 to 0.07 mgm/kg body weight, 1 to 3 times daily.

The following examples illustrate a few pharmaceutical dosage unit compositions comprising a compound of the present invention as an active ingredient and represent the best modes contemplated of using the invention. The parts are parts by weight unless otherwise specified.

EXAMPLE 51

Coated tablets

The tablet core composition is compounded from the following ingredients:

| | |
|---|---|
| 2-Amino-7-ethyl-6,7,8,9-tetrahydro-5H—pyrazino[2,3-d]azepine hydrochloride | 5.0 parts |
| Lactose | 33.5 parts |
| Corn starch | 10.0 parts |
| Gelatin | 1.0 parts |
| Magnesium stearate | 0.5 parts |
| Total | 50.0 parts |

Preparation:

The active ingredient, the lactose and the corn starch are intimately admixed with each other, the mixture is moistened with an aqueous 10% solution of the gelatin, the moist mass is granulated through a 1 mm-mesh screen, and the granulate is dried at 40° C. and again passed through the screen. The dry granulate is admixed with the magnesium stearate, and the composition is compressed into 50 mgm-tablet cores. The entire procedure must be carried out in a darkened room. The tablet cores are subsequently coated with a thin shell consisting essentially of a mixture of sugar and talcum and then polished with beeswax. Each coated tablet is an oral dosage unit composition containing 5 mgm of the active ingredient.

EXAMPLE 52

Suppositories

The suppository composition is compounded from the following ingredients:

| | |
|---|---|
| 2-Amino-7-methyl-6,7,8,9-tetrahydro-5H—pyrazino[2,3-d]azepine dihydrochloride | 10.0 parts |
| Suppository base (e.g. cocoa butter) | 1,690.0 parts |
| Total | 1,700.0 parts |

Preparation:

The finely powdered active ingredient is homogeneously blended with the aid of an immersion homogenizer into the suppository base which had previously been melted and cooled to 40° C., and 1700 mgm-portions of the composition are poured at 37° C. into cooled suppository molds and allowed to harden therein. Each suppository is a rectal dosage unit composition containing 10 mgm of the active ingredient.

EXAMPLE 53

Hypodermic solution

The solution is compounded from the following ingredients:

| | |
|---|---|
| 2-Amino-7-allyl-6,7,8,9-tetrahydro-5H—pyrazino[2,3-d]azepine dihydrochloride | 5.0 parts |
| Citric acid | 7.0 parts |
| Sec. sodium phosphate .2H$_2$O | 3.0 parts |
| Sodium pyrosulfite | 1.0 parts |
| Distilled water q.s.ad | 1000.0 parts by vol. |

Preparation:

The buffers, the active ingredient and the sodium pyrosulfite are dissolved in a sufficient amount of distilled water which had previously been boiled and cooled in an atmosphere of carbon dioxide. The solution is diluted to the indicated volume with additional boiled distilled water, and the solution is filtered until free from pyrogens. The filtrate is filled into 1 cc-brown ampules in an atmosphere of an inert gas, and the filled ampules are sterilized for 20 minutes at 120° C. The entire procedure must be performed in a darkened room.

The contents of each ampule are an injectable solution containing 5 mgm of the active ingredient.

EXAMPLE 54

Drop solution

The solution is compounded from the following ingredients:

| | |
|---|---|
| 2-Amino-7-ethyl-6,7,8,9-tetrahydro-5H—pyrazino[2,3-d]-azepine dihydrochloride | 0.5 parts |
| Methyl p-hydroxy-benzoate | 0.035 parts |
| Propyl p-hydroxy-benzoate | 0.015 parts |
| Oil of anise | 0.05 parts |
| Menthol | 0.06 parts |
| Ethanol, pure | 10.0 parts |
| Citric acid | 0.7 parts |
| Sec. sodium phosphate .2H$_2$O | 0.3 parts |
| Sodium cyclamate | 1.0 parts |
| Glycerin | 15.0 parts |
| Distilled water q.s.ad | 100.0 parts by vol. |

Preparation:

The p-hydroxy benzoates, the oil of anise and the menthol are dissolved in the ethanol (solution I).

The buffers, the active ingredient and the sodium cyclamate are dissolved in a sufficient amount of distilled water, and the glycerin is added thereto (solution II).

Solution I is stirred into solution II, and the mixed solution is diluted to the indicated volume with additional distilled water and then filtered. The filtrate is filled into 100 cc-bottles equipped with a dropping spout. The preparation and bottling of the solution must be carried out in an atmosphere of an inert gas. 1 ml of the solution (about 20 drops) is an oral dosage unit composition containing 5 mgm of the active ingredient.

Any one of the other compounds embraced by formula I or a non-toxic, pharmacologically acceptable acid addition salt thereof may be substituted for the particular active ingredient in Examples 51 through 53. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

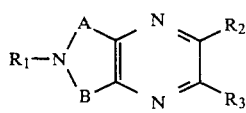

wherein

A and B are each ethylene or (alkyl of 1 to 3 carbon atoms)-ethylene;

R$_1$ is hydrogen, alkyl of 1 to 6 carbon atoms, cycloalkyl of 3 to 7 carbon atoms, alkenyl of 3 to 6 carbon atoms, phenyl-(alkyl of 1 to 3 carbon atoms), halophenyl-(alkyl of 1 to 3 carbon atoms), alkanoyl of 1 to 3 carbon atoms, phenyl-(alkanoyl of 1 to 3 carbon atoms), halophenyl-(alkanoyl of 1 to 3 carbon atoms), alkoxycarbonyl of 2 to 4 carbon atoms, aralkoxycarbonyl of 8 to 10 carbon atoms or phenyl;

one of R$_2$ and R$_3$ is amino, and the other is hydrogen, chlorine, bromine, alkyl of 1 to 3 carbon atoms, alkoxy of 1 to 3 carbon atoms, alkoxycarbonyl of 2 to 4 carbon atoms, phenyl or halophenyl;

or a non-toxic, pharmacologically acceptable acid addition salt thereof.

2. A compound of claim 1, where

A and B are each ethylene or methyl-ethylene;

R$_1$ is hydrogen, alkyl of 1 to 4 carbon atoms, allyl, cycloalkyl of 3 to 6 carbon atoms, phenyl-(alkyl of 1 to 3 carbon atoms), chlorophenyl-(alkyl of 1 to 3 carbon atoms), formyl, phenyl-formyl, chlorophenyl-formyl, acetyl, phenyl-acetyl, chlorophenyl-acetyl, ethoxy-carbonyl or phenyl;

R$_2$ is hydrogen, chlorine, bromine, methyl, ethyl, methoxy, phenyl or ethoxycarbonyl; and R$_3$ is amino;

or a non-toxic, pharmacologically acceptable acid addition salt thereof.

3. A compound of claim 1, where

A and B are ethylene;

R$_1$ is methyl, ethyl, isopropyl, cyclopropyl, cyclobutyl or allyl;

R$_2$ is methyl, hydrogen, chlorine or bromine; and

R$_3$ is amino;

or a non-toxic, pharmacologically acceptable acid addition salt thereof.

4. A compound of claim 1, where

A and B are ethylene;

R$_1$ is methyl, ethyl, isopropyl, cyclopropyl, cyclobutyl or allyl;

R$_2$ is hydrogen; and

R$_3$ is amino;

or a non-toxic, pharmacologically acceptable acid addition salts thereof.

5. A compound of claim 1, which is 2-amino-7-ethyl-6,7,8,9-tetrahydro-5H-pyrazino[2,3-d]azepine or a non-toxic, pharmacologically acceptable acid addition salt thereof.

6. A compound of claim 1, which is 2-amino-7-methyl-6,7,8,9-tetrahydro-5H-pyrazino[2,3-d]azepine or a non-toxic, pharmacologically acceptable acid addition salt thereof.

7. A bradycardiac pharmaceutical dosage unit composition consisting essentially of an inert pharmaceutical carrier and an effective bradycardiac amount of a compound of claim 1.

8. The method of slowing the heart rate of a warm-blooded animal in need thereof, which comprises perorally, parenterally or rectally administering to said animal an effective bradycardiac amount of a composition of claim 7.

* * * * *